United States Patent [19]
Acciai et al.

[11] Patent Number: 6,056,187
[45] Date of Patent: May 2, 2000

[54] MODULAR WIRE BAND STENT

[75] Inventors: Michael Acciai, Newark Valley; Richard Ronald Hall, Endwell; John Thomas Legg, Glen Aubrey, all of N.Y.

[73] Assignee: International Business Machines Corporation, Armonk, N.Y.

[21] Appl. No.: 09/113,679

[22] Filed: Jul. 10, 1998

Related U.S. Application Data

[62] Division of application No. 08/670,080, Jun. 25, 1996, Pat. No. 5,855,596.

[51] Int. Cl.$^7$ ..................................................... B23K 31/02
[52] U.S. Cl. .................... 228/173.5; 228/212; 156/304.2
[58] Field of Search ................................. 228/170, 173.5, 228/182, 185, 212; 156/258; 304/304.2

[56] References Cited

U.S. PATENT DOCUMENTS

| | | |
|---|---|---|
| 4,656,860 | 4/1987 | Orthuber et al. . |
| 5,019,090 | 5/1991 | Pinchuk . |
| 5,104,404 | 4/1992 | Wolff . |
| 5,170,654 | 12/1992 | Anagnostopoulos . |
| 5,217,483 | 6/1993 | Tower . |
| 5,282,824 | 2/1994 | Gianturco . |
| 5,304,200 | 4/1994 | Spaulding . |
| 5,314,472 | 5/1994 | Fontaine . |
| 5,370,683 | 12/1994 | Fontaine . |
| 5,382,261 | 1/1995 | Palmaz . |
| 5,383,892 | 1/1995 | Cardon et al. . |
| 5,411,552 | 5/1995 | Andersen et al. ........................... 623/2 |
| 5,443,496 | 8/1995 | Schwartz et al. . |
| 5,578,149 | 11/1996 | Scheerder et al. ....................... 148/563 |
| 5,591,197 | 1/1997 | Orth et al. . |
| 5,591,198 | 1/1997 | Boyle et al. . |
| 5,716,396 | 2/1998 | Williams, Jr. ............................... 623/1 |
| 5,800,519 | 9/1998 | Sandock ..................................... 623/1 |

FOREIGN PATENT DOCUMENTS

| | | |
|---|---|---|
| 0 423 916 A1 | 4/1991 | European Pat. Off. . |
| 0 540 290 A2 | 5/1993 | European Pat. Off. . |

*Primary Examiner*—Samuel M. Heinrich
*Attorney, Agent, or Firm*—Lawrence R. Fraley

[57] ABSTRACT

A radially expandable device particularly adaptable for use as an endoprothesis is described along with a method of fabrication. The method begins by obtaining a number of individual, separate generally circular hoops by a number of ways, such as cutting a length of wire, forming it into a generally circular loop, and attaching the ends together. In another aspect of this method of fabrication, the individual, separate generally circular hoops are obtained by cutting the needed number from a tubing. Thereafter, a wave-like pattern is formed in each hoop, with a die, in a direction transverse the axis of the wire, creating a predetermined number of rings and attaching them at the crest point to form a stent that can be compressed for inserting into a lumen where it can be expanded to provided a needed support.

25 Claims, 1 Drawing Sheet

MODULAR WIRE BAND STENT

This application is a division of U.S. Ser. No. 08/670,080, filed Jun. 25, 1996, now U.S. Pat. No. 5,855,596.

BACKGROUND OF THE INVENTION

1. Field of the Invention

The present invention, generally, relates to a device that is useful for endoprosthesis purposes and is commonly identified as a stent, and more particularly, it relates to a new and improved method of fabricating a stent.

A stent is particularly useful in the medical field of angioplasty involving the reconstruction of vessels that carry blood in both humans and animals. The stent is used to maintain such blood vessels, structurally, in a clear and open condition.

2. State of the Art

The methods used today to fabricate stents are difficult to perform, are difficult to form stents with consistent structural torsional and radial stiffness and involve high costs. They are formed of tantalum or stainless steel in complex configurations that can produce a work-hardened crystallization in the metal.

U.S. Pat. No. 5,370,683 to Fontaine describes a stent formed of a single filament wrapped around a mandril with a series of U-shaped bends.

U.S. Pat. No. 5,304,200 to Spaulding describes a method of making stents involving winding an elongated strand forming a helix like structure with the ends welded to an adjacent section.

U.S. Pat. No. 5,217,483 to Tower describes a stent arranged to have U-shaped sections formed in a continuous wire with two ends and with the ends attached together to prevent axial expansion.

For a stent to achieve maximum usefulness, it must be flexible in a bending mode during insertion, and it must exhibit stiffness in both torsional and radial modes in order to provide support. To fabricate stents today, wire is fed continuously from a spool and is formed into a generally sinusoidal configuration.

Then, the wire in this sinusoidal configuration is wound around a mandrel in order to produce a helical arrangement. Next, the crests and troughs in this helical arrangement are pressed together so that they touch at this point, and they are welded to provide the required supporting structure.

The stents today are formed into the required configuration to permit a high level of plastic deformation to be achieved during their use. However, the bending and other deformations of the wire followed by the heating and cooling encountered during the welding produces a condition within the metal wire known as work hardening, which lessens much of the wire's ability to provide support in use.

During use, a stent is in a compressed condition, first. Then, a deflated angioplasty balloon is fed inside the compressed stent. This assembly is inserted into a patient's blood vessel, usually an artery, and moved into position. The balloon is inflated to enlarge the stent to a desired diameter, after which the balloon is removed.

The stent within an artery, or within any other type of vessel, is exposed to repetitive flexing as a part of a circulatory system, both from the systolic and the diastolic variations in blood pressure and from variations in movement of a body. Such loading and unloading of a metallic article can produce further work-hardening of the metal, causing premature failure of support.

Methods of fabrication of stents in the past have produced an aspect of this work-hardening caused by the crystallization within the metallic wire, from the heating and cooling cycles during the prior fabrication processes. Moreover, a stent fabrication method is needed that permits more consistency in stiffness.

OBJECTS AND SUMMARY OF THE INVENTION

A principal object of the present invention is to provide a new and improved configuration for a stent.

It is also an object of the present invention to provide a method of fabricating stents that lessen, if not overcome entirely, the disadvantages of prior stents.

A further object of the present invention is to provide a new and improved configuration for a stent that admits of a fabrication method to achieve increased uniformity in stiffness.

A still further object of the invention is to provide a method of fabricating stents that can achieve a reduction in cost.

Another object of the present invention is to provide a method of fabricating stents to produce improvement in the integrity of the welds.

Briefly, an assembly for use as a stent includes at least two cylinders defined by wire that is bent in a predetermined pattern and arranged to form the surface of the cylinders. The cylinders of the wire patterns are shifted circumferentially until maximum and minimum edges in adjacent wire patterns are positioned adjacent each other, and predetermined ones of these edges are attached to form the assembly.

DETAILED DESCRIPTION OF THE INVENTION

Figure 1:
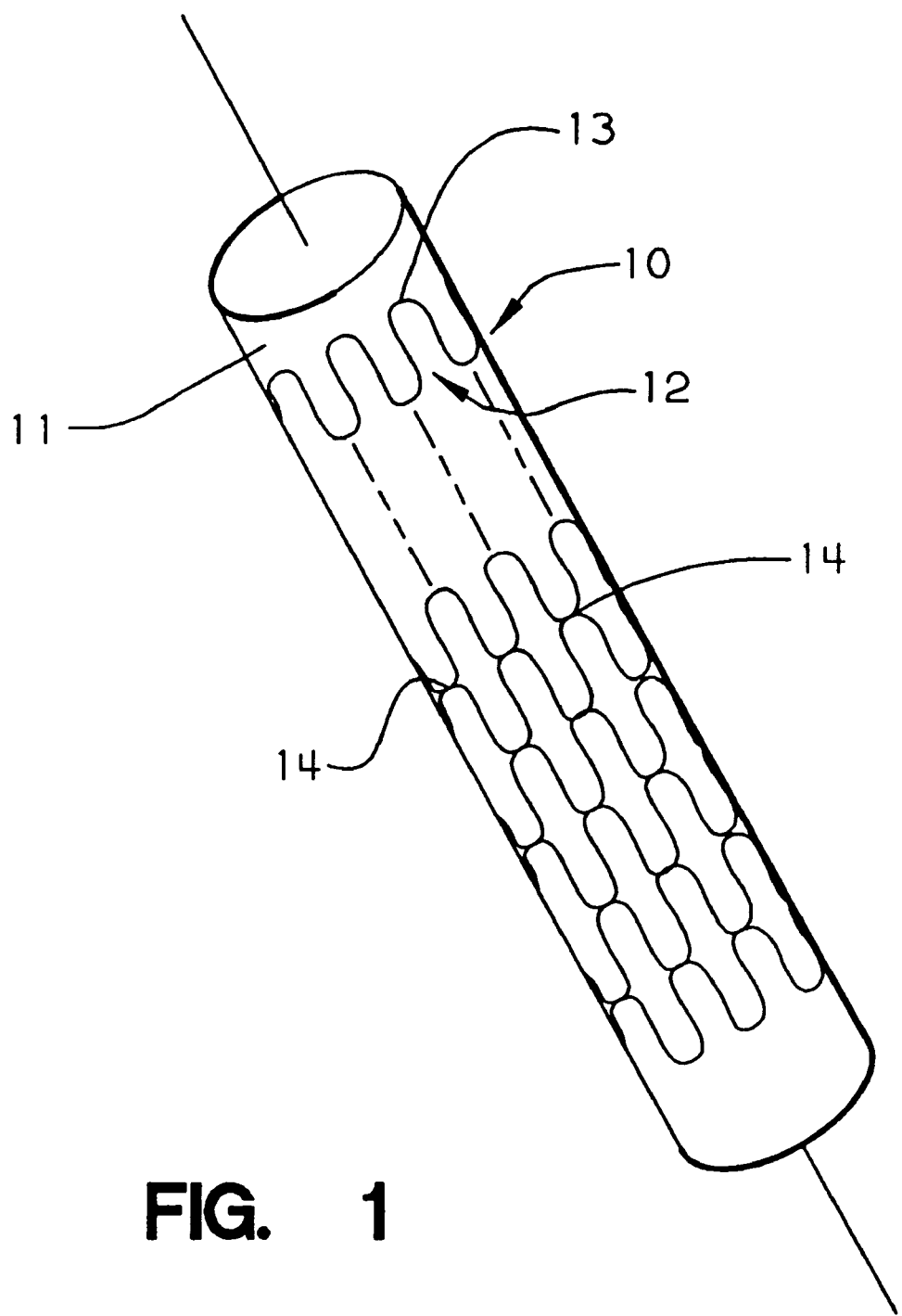
FIG. 1 is an illustration of a stent that is fabricated by the method of the invention and is useful as an aid in describing the method of fabrication.

To fabricate a stent in accordance with the present invention, a configuration is determined first, which includes the length and the diameter. These are features that customarily are dictated by the lumen in which the stent is to be used.

Next, a pattern of waves is determined, which takes into consideration a manner in which the stent is to be compressed. This is the state of a stent that it customarily exhibits for it to be inserted through an incision into a lumen. Therefore, the particulars of the intended use of a stent will determine the amount of compression that a stent must tolerate without deformation.

It is at this point in the fabrication of a stent that the present invention deviates so drastically from prior practices. For example, in accordance with the invention, the filament wire, which is quite small, in the order of 0.05 millimeters in diameter, is unwound from a spool source and is cut in predetermined lengths.

Each of these lengths is formed into a circular hoop by winding each pre-cut length of filament about a mandril of the desired diameter, and the two ends of the filament are attached together. Usually, it might be expected that a welded joint will be formed to attach the ends together, and this will take into consideration the type of metal selected.

The types of metal that will be selected can include one of a group of precious metals like gold or silver, or it can include tantalum, or even stainless steel, or any combination, so long as the metal type is compatible biologically with the anticipated environment of use. A particularly desirable characteristic of the type of metal from which a stent is formed is that it should be capable of maintaining the shape or state in which it is bent.

Next, each individual ring is formed with a wave pattern in a direction parallel to an axis through the center of the ring. This is illustrated in FIG. 1 of the drawings in which the ring is identified generally by the reference numeral 10.

Actually, as a practical matter, the pattern selected can be any wave-like pattern, and the term sinusoidal is used here to identify this pattern. A principal purpose of any such pattern is to render the ring 10 flexible, i.e., compressible and expandable and to provide support for the lumen.

It is convenient to identify the location of the pattern as defining a cylinder, in effect, that has a surface coinciding with the outer surface of a mandril 11.

In accordance with one form of the invention, a number of the rings 10 are fitted on a mandril, such as the mandril 11 in the drawings. The number of the rings 10 will be determined by the length of the resulting stent needed, which will be determined by the depth of each trough 12 and the height of each crest 13 in the ring 10.

The troughs 12 and the crests 13 are formed by dies with a predetermined configuration. Then, according to the method of the present invention, a number of the rings 10 are positioned on a mandril 11 with the crest 13 of one ring located adjacent the crest 13 of the next ring 10 to form a stent with a required length.

The fabrication of the stent is completed by micropositioning each ring 10 with the adjacent ring 10 and attaching them at this point, identified by the numeral 14 in the drawings.

A preferred form of the above method is as follows: Wire (or "filament", as it may be termed) is fed from a bulk wire storage spool and is cut in a predetermined length. The wire thus cut is formed into a circular hoop. The ends of the wire are restrained in this contiguous position, which can include welding.

Dies form the hoop into a circular ring having a series of sinusoidal troughs and crests. The ring thus formed is slipped onto a mandril and clamped in a location.

Another wire or filament is fed from the storage spool and is cut in the same length, formed into the circular hoop with its ends restrained as previously. After the sinusoidal trough-and-crest pattern, this circular ring is slipped onto the mandril and positioned with the crests aligned contiguously with the crests of the adjacent circular ring.

Predetermined ones of these aligned and contiguous crests are attached, such as by welding. Next, after the selected crests are attached, another length of wire or filament is fed from the spool source, is cut and formed into a circular hoop with the two ends aligned and attached, the sinusoidal trough-and-crest pattern is formed, the ring is slipped onto the mandril, the ring is adjusted circumferentilly to align its crests with those of the previous ring, and preselected ones are welded. This sequence of steps is repeated until a stent with a desired length is obtained. In this presently preferred form of the invention, the sinusoidal pattern includes cycles in a range from 6 to 21 cycles.

Although the step of attaching the two ends together is necessary when the wire is cut in lengths, as described above, it can be avoided, according to another aspect of the invention, by selecting (or fabricating) a tube of a desired material having a diameter already of the hoop described above. The circular hoop, then, is obtained by cutting a portion from the selected (or fabricated) tube.

Thereafter, the circular ring with the troughs and crests described, supra, is formed without a weld or other attachment steps for ends of a filament. Of course, any method may be used for fabricating the tube from which hoops may be cut, including machining, casting, forging, etc.

While a presently preferred form of the invention has been described to illustrate the principles involved, the description is not intended as limiting in any way, but rather, it is intended to be illustrative of those principles. Therefore, the present invention is intended to embrace all modifications, alternatives and variations that fall within the scope and the spirit of the appended claims.

What is claimed is:

1. A process for forming a radially expandable device, particularly adaptable for use as an endoprothesis, comprising:

cutting a plurality of wires of predetermined material and dimensions into predetermined lengths;

bending said wires into substantially circular shapes, and affixing their ends together;

forming said substantially circular shaped wires into a predetermined generally sinusoidal pattern with the pattern creating maximum and minimum points defining the surfaces of cylinders about an axis;

aligning a predetermined number of said cylinders with their axes co-extensive;

shifting said cylinders circumferentially so that a maximum point of said pattern on one cylinder is contiguous with a minimum point on an adjacent cylinder;

affixing predetermined ones of said contiguous points to form said device.

2. The process of claim 1 including the step of forming said wires of non-corrosive material.

3. The process of claim 1 including the step of selecting wires of about 5 mils in diameter and having a generally round configuration.

4. The process of claim 1 including the step of forming said wires of a stainless steel material.

5. The process of claim 1 including the step of using a tantalum material for said wires.

6. The process of claim 1 including the step of welding said predetermined contiguous points of adjacent patterns.

7. The process of claim 1 including the step of affixing alternate ones of said contiguous points.

8. The process of claim 1 including the step of affixing alternate ones of said contiguous points by welding.

9. The process of claim 1 wherein said generally sinusoidal pattern includes cycles within the range of 6 to 21 cycles.

10. A process for forming a radially expansible device that is particularly adaptable for use as an endoprothesis, comprising:

(a) cutting a predetermined length of a filament from a source, and bending it to form a substantially circular hoop with two adjacent ends;

(b) affixing said two adjacent ends together to form a continuous loop in said substantially circular hoop;

(c) forming a predetermined pattern creating troughs and crests laterally of said filament defining a cylinder surface;

(d) fitting said filament with said pattern on a mandril to a predetermined position;

(e) repeating said steps (a) through (d) creating a second continuous loop of said filament with a pattern of troughs and crests on said mandril; and (f) affixing predetermined crests on said second continuous loop with crests on said first mentioned continuous loop to form said radially expandable device.

11. The process of claim 10 wherein said step of cutting a length of a filament includes selecting a material for said filament.

12. The process of claim 10 wherein said step of cutting a length of a filament includes selecting tantalum as a material of which said filament is formed.

13. The process of claim 10 wherein said step of cutting a length of a filament includes selecting stainless steel as a material of which said filament is formed.

14. The process of claim 10 wherein said step of cutting a length of a filament includes selecting a non-corrosive material of which said filament is formed.

15. The process of claim 10 wherein said step of cutting a length of a filament includes selecting a filament that is circular with a predetermined stiffness.

16. The process of claim 10 including the step of selecting generally sinusoidal as said predetermined pattern.

17. The process of claim 10 wherein said predetermined pattern includes cycles within the range of 6 to 21 cycles.

18. The process of claim 10 wherein said affixing said two adjacent ends includes the step of welding.

19. The process of claim 10 wherein said step of repeating said steps (a) through (d) creating a second continuous loop includes repeating said steps a predetermined number of times to create a plurality of said continuous loops.

20. The process of claim 10 including the step of creating a plurality of said continuous loops, each of said loops having two ends, and welding each of said ends with an adjacent end.

21. A method of fabricating a radially expandable device that is particularly adaptable for use as an endoprothesis, comprising the steps of:

(a) cutting a predetermined length from a tube of a predetermined diameter and material a substantially circular hoop;

(b) forming in said circular hoop a predetermined pattern creating troughs and crests laterally defining a cylinder surface;

(c) fitting said circular hoop with said pattern on a mandril to a predetermined position;

(d) repeating said steps (a) through (c) creating a second circular hoop with a pattern of troughs and crests on said mandril; and (e) affixing predetermined crests on said second circular hoop with crests on said first mentioned circular hoop to form said radially expandable device.

22. The method of claim 21 wherein said predetermined length cut from said tube is in the order of 5 mils.

23. The method of claim 21 wherein said predetermined material of said tube is stainless steel.

24. The method of claim 21 wherein said predetermined material of said tube is tantalum.

25. The method of claim 21 wherein said steps (a) through (e) are repeated a predetermined number of times forming said expandable device with a predetermined length.

* * * * *